United States Patent
Szaro et al.

(10) Patent No.: US 7,776,794 B2
(45) Date of Patent: Aug. 17, 2010

(54) BIOSENSOR USING LIVING CELLS ON SILICON-BASED MICROARRAYS

(75) Inventors: Ben G. Szaro, Albany, NY (US); James Castracane, Albany, NY (US); Xiaojun Feng, Albany, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 10/945,563

(22) Filed: Sep. 20, 2004

(65) Prior Publication Data

US 2005/0095630 A1    May 5, 2005

Related U.S. Application Data (60) Provisional application No. 60/504,538, filed on Sep. 19, 2003.

(51) Int. Cl.
*C40B 30/06* (2006.01)
*C40B 40/02* (2006.01)
*C12N 5/00* (2006.01)
*C12N 5/02* (2006.01)

(52) U.S. Cl. .................... 506/14; 506/10; 435/325

(58) Field of Classification Search ............ 435/176, 435/7.21, 325; 428/451; 324/692; 506/14, 506/10
See application file for complete search history.

(56) References Cited

U.S. PATENT DOCUMENTS 5,134,070 A * 7/1992 Casnig .................. 435/173.6

FOREIGN PATENT DOCUMENTS

EP    219626 A2 *    4/1987

OTHER PUBLICATIONS

Hediger et al, Fabrication of a novel microsystem of for the electrical characterisation of cell arrays. Sensors and Actuators. B. 1999. vol. 56: 175-180.*
Chang et al. Constitutive secretion of exogenous neurotransmitter by nonneuronal cells: implications for neuronal secretion. Biophysical Journal. vol. 75: 1354-1364. 1998.*
Gillis et al. A novel microfabricated device to measure hormone/neurotransmitter release with millisecond temporal resolution. Proceedings of SPIE. vol. 378-382. Jun. 2002.*
Chen et al. Amperometric detection of quantal catecholamine secretion from individual cells on micromachined silicon chips. Analytical Chemistry. vol. 75: 518-524. Dec. 18, 2002 on Web.*
Wolf et al., Science. vol. 144: 1578-1580; 1964.*

* cited by examiner

*Primary Examiner*—Sue Liu
(74) *Attorney, Agent, or Firm*—Heslin Rothenberg Farley & Mesiti; Kathy Smith Dias (57) ABSTRACT

The invention relates to a biosensor comprising living cells that express a chemosensor, or receptor, on their surface. When grown on a microarray comprising electrodes, the cells can be induced, by binding of a ligand to the receptor, to secrete a molecule. This secretion event is detected with millisecond temporal resolution via electrochemical oxidation of the secreted molecule on the electrode which is voltage-clamped slightly above its redox potential. The current so generated is indicative of the amount of the ligand bound to the receptor.

15 Claims, 10 Drawing Sheets

BIOSENSOR USING LIVING CELLS ON SILICON-BASED MICROARRAYS

CROSS REFERENCE TO RELATED APPLICATIONS

This application is a non-provisional application claiming priority to U.S. provisional application Ser. No. 60/504,538 filed Sep. 19, 2003, the disclosure of which is hereby incorporated by reference.

FIELD OF THE INVENTION

The invention relates to cell-based biosensors, a process for producing a biosensor and a method of detecting small amounts of analyte in a biological sample.

BACKGROUND OF THE INVENTION

Microfabrication techniques originally developed for the semiconductor industry afford the opportunity to design microarray devices that, when used in conjunction with living cells as chemosensors, allow analyte detection that is extremely sensitive and can be highly automated. Furthermore, the devices can be mass produced at low cost.

Living cells are perfect chemosensors due to their exquisite sensitivity to a variety of complex chemical compounds. Ligand binding to G-protein coupled receptors (GPCR) activates enzymatic cascades that amplify the signal, enabling cells to respond to minute quantities of ligand. These cascades also direct the stimulus to a specific cellular response. In insects, for example, pheromone, odorant and taste receptive GPCRs activate phospholipase C (PLC), which releases inositol 1,4,5-triphosphate ($IP_3$) and diacylglycerol through hydrolysis of phosphatidyl inositol 4,5 bisphosphate. $IP_3$ production in turn releases $Ca^{+2}$ from intracellular stores, instigating a rise that then triggers a variety of cellular responses, including the stimulation of cellular secretion through exocytosis.

As another example, endocrine cells and nerve cells secrete hormone and neurotransmitter, respectively, by a regulated secretory pathway in which an increase in intracellular $Ca^{++}$ concentration triggers the fusion of hormone-containing membrane vesicles with the plasma membrane releasing hormone.

SUMMARY OF THE INVENTION

In principle, a cell-based chemical detector can be made by monitoring any of the downstream links in the chain of events triggered by binding of ligand to receptor. The present invention exploits the cellular characteristics described above by integrating cells into a device for the detection of biologically active molecules based on the ability of a receptor on the surface of the cell to bind the molecule and induce secretion by the cell of another, oxidizable molecule.

In one aspect, therefore, the invention relates to a biosensor comprising (a) a microarray adapted to support cell growth, and having electrodes patterned thereon; (b) live cells that express a chemosensor receptor wherein the cells are grown on the surface of the microarray, and, in response to ligand binding to the receptor, the cells secrete a molecule that is oxidized on the electrode generating a detectable current; and (c) a detector adapted to detect current generated by the microarray.

In a related aspect, the present invention relates to a method of measuring an analyte in a biological sample comprising: (a) exposing the biosensor of the invention to a biological sample; and (b) detecting a signal generated as the result of exposure of the biosensor to the biological sample, wherein said signal is indicative of the amount of analyte in the biological sample.

DETAILED DESCRIPTION OF THE INVENTION

All patents, applications, publications and other references cited herein are hereby incorporated by reference into the present disclosure.

In practicing the present invention, many conventional techniques in semiconductor fabrication, molecular and cellular biology, and recombinant DNA technology are used. Such techniques are well known and are explained in, for example, Sambrook et al., 2001, *Molecular Cloning: A Laboratory Manual*, Third Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins, eds.); *Transcription and Translation*, 1984 (Hames and Higgins, eds.); *A Practical Guide to Molecular Cloning*; the series, *Methods in Cell Biology*, Volume 36 (edited by Brian K. Kay and H. Benjamin Peng, Academic Press, New York, 1991); and *Basic Methods in Molecular Biology* (L. Davis, M. Kuehl, J. Battey, eds., Appleton and Lange, Norwalk Conn., 1994); *Current Protocols in Molecular Biology*, John Wiley & Sons, Inc. (1994), and all more current editions of these publications.

In the description that follows, certain conventions will be followed as regards the usage of terminology.

The term "biosensor" refers to a device comprising living cells which provide a measurable output in response to an external stimulus, for example binding of a chemical ligand to a membrane-bound receptor.

The term "chemosensor receptor" refers to any cell surface receptor, for example, a G protein-coupled receptor (GPCR) that binds a ligand activating phospholipase C to raise intracellular calcium. Examples include, but are not limited to, receptors for bombesin, gastrin releasing peptide, neuromedin B, angiotensin, bradkinin, anaphylatoxin, formyl peptide, interleukin 8, cholecystokinin, gastrin, endothelin 1, neurotensin, substance P, substance K, neuromedin K, oxytocin, vasopressin, thrombin, orexin (hypocretin), urotensin, prostaglandin F2-2, ATP, platelet activating factor, gonadotropin releasing hormone, thyrotropin releasing hormone, glutamate, epinephrine, norepinephrine, histamine, serotonin and many others.

Also encompassed by the present invention are receptors that are recombinantly modified by site-directed mutagenesis or domain swapping to generate a receptor wherein binding of ligand activates phospholipase C to increase concentrations of intracellular calcium.

The term "detector" refers to a device suitable for amperometric detection which is adapted to detect current generated by the microarray. Detectors suitable for use in the present invention are well known in the art.

Through G protein-coupled receptors (GPCR), living cells can accurately discriminate among chemically similar compounds, enabling them to detect complex biomolecules at exquisitely low thresholds. The biosensor of the present invention exploits this capacity by taking cells that express an endogenous G protein-coupled receptor (GPCR), such as the ATP receptor, or cells that have been modified to express an exogenous G protein-coupled receptors and growing them on microarrays for subsequently exposing them to a sample containing potential ligands, or agonists of the receptor. The biosensor of the present invention therefore, comprises cells that either constitutively express or which have been transfected with a G protein-coupled receptor that will, upon ligand binding, be stimulated to secrete a detectable molecule.

The biosensor of the invention, therefore, provides a mechanism for detecting complex biologically relevant compounds in solution. Furthermore, the biosensors of the present invention may be employed in a screening process for compounds which bind a receptor of interest and which activate (agonists) or inhibit activation (antagonists) of the receptor.

To create the biosensor of the invention, a cell that is amenable to recombinant alteration is modified to express a chemosensor receptor, for example, a G protein-coupled receptor. The transfected cells are then grown directly on the surface of a microarray with patterned electrodes (shown in FIG. 1). Alternatively, a cell that expresses an endogenous receptor, for example, the ATP receptor, may be used.

After integration into a standard DIP package, the appropriate pins of the chip carriage are then connected to the headstage of a detector. The microarrays may optionally be inserted into a breadboard that is mounted on the moveable stage of an upright microscope, which allows cells to be observed during testing.

The cells, which have grown to become a confluent monolayer on the surface of the microarray, are "pre-loaded" with medium containing the appropriate amount of an oxidizable molecule, for example, 0.5-10 mM of a catecholamine such as norepinephrine (NE), for a time sufficient for the cells to endocytose the catecholamine, about 1-30 minutes. The pre-loading medium is then replaced with fresh medium, and the solution is grounded with a Ag/AgCl wire.

A voltage of about 700 mV is then applied to the active electrode and amperometric current is recorded using a suitable detector, for example, the Keithley Model 238 (Keithley Instruments, Inc., Cleveland Ohio), and recorded on a PC using Labview 5.1 (National Instruments, Austin, Tex.) or comparable data management software.

Figure 4:
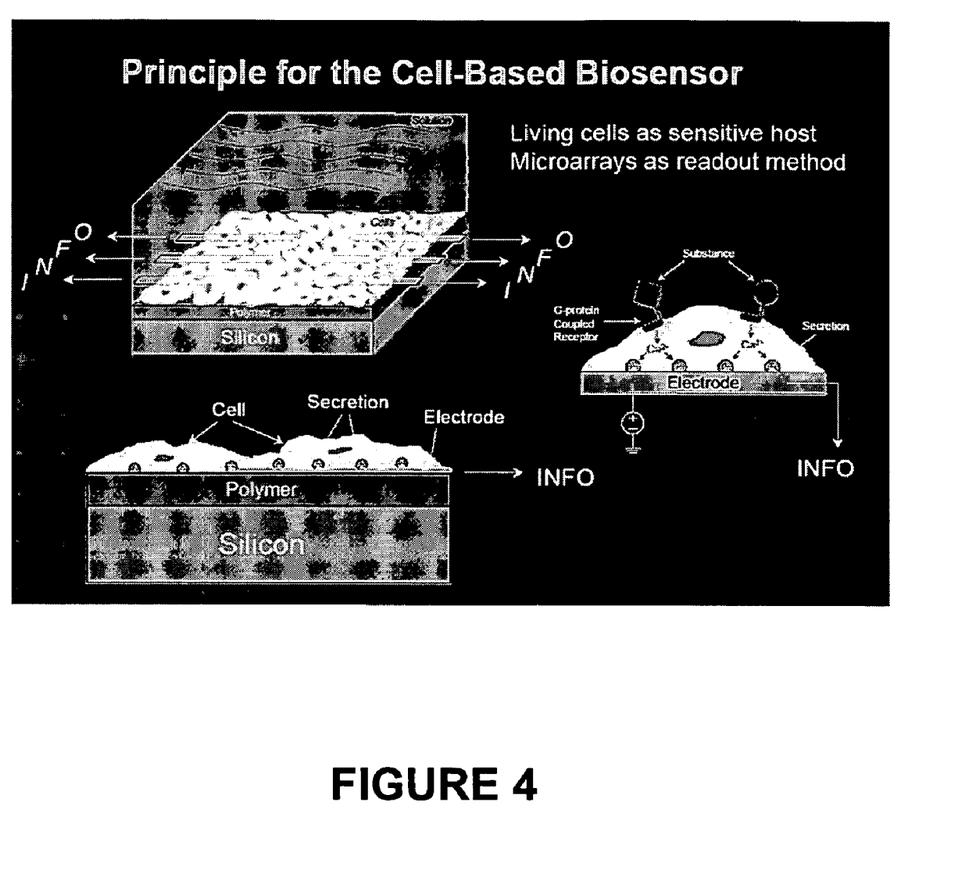
FIG. 4 is a schematic representation of the underlying mechanism of the cell-based biosensor of the present invention.

Within minutes of pre-loading, the cells are then exposed to a biological sample containing an analyte, the detection of which is desired. Binding of analyte to a receptor on the cells' surface increases intracellular calcium, thereby stimulating release of the pre-loaded NE. This secretion event is detected with millisecond temporal resolution via electrochemical oxidation of the secreted compound on an electrode that is voltage-clamped slightly above its redox potential. Increases in current due to oxidation of NE on the Cr/Au electrode is recorded. This is represented schematically in FIG. 4.

Fabrication of Microarray

Fabrication of a microarray device of the biosensor of the present invention is in accordance with techniques well known to those of skill in the semiconductor arts. The surface of the silicon-based microarray comprises a material which will support cell growth, for example, polyimide, polydimethylglutarimide (PMGI), or silicon dioxide ($SiO_2$).

Electrodes may be fabricated from any suitable electrically conductive material that is compatible with living cells. Suitable materials include noble metals (including gold, platinum, and palladium), refractory metals (including titanium, tungsten, molybdenum, and iridium), corrosion-resistant alloys (including stainless steel) and carbon or other organic conductors (including graphite and polypyrrole) with Cr/Au electrodes being preferred. The number and size of electrodes will vary, with the objective of increasing the electrode surface to maximize current without interfering with cell growth.

Figure 3:
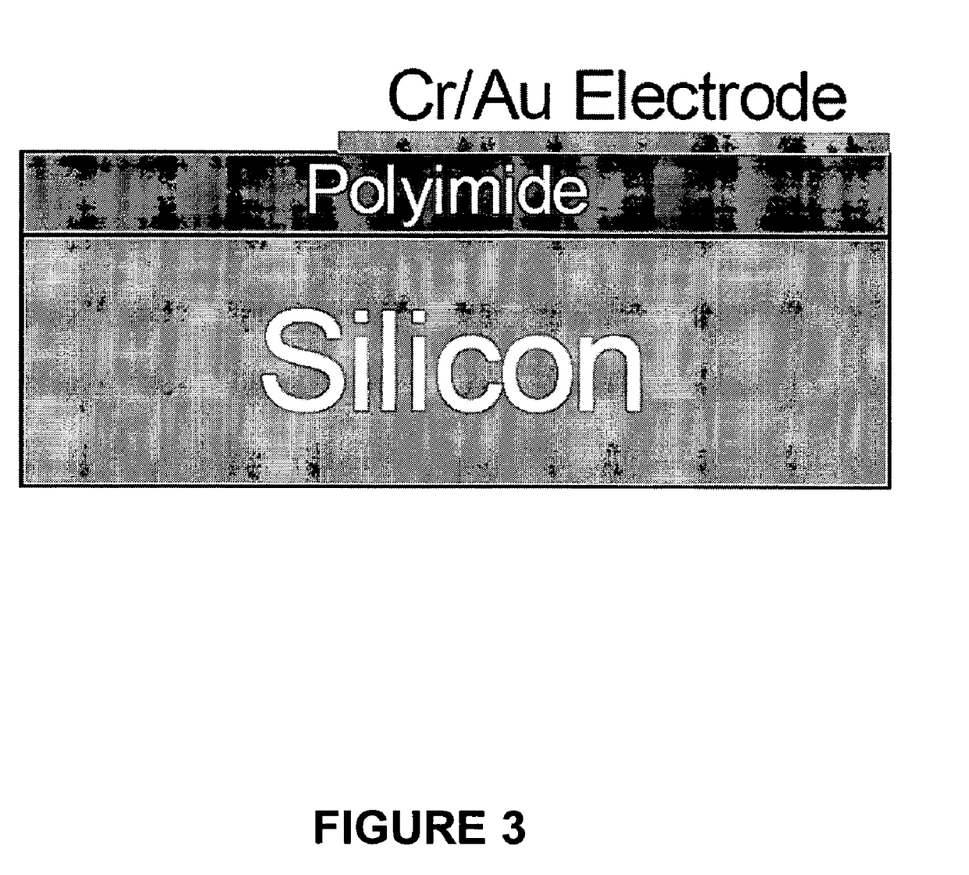
FIG. 3 is a schematic diagram of one embodiment of a microarray device in cross section, illustrating the position of the Cr/Au electrode above the polyimide surface bound to the underlying silicon test wafer.

In one embodiment, the biosensor comprises a silicon-based microarray comprising a polyimide surface that is used to support cell growth. The microarray incorporates Cr/Au electrodes to oxidize and detect molecules secreted by the cells (FIG. 3). As will be discussed below, the microarrays described herein can support confluent growth of some cell types at room temperature.

Figure 1:
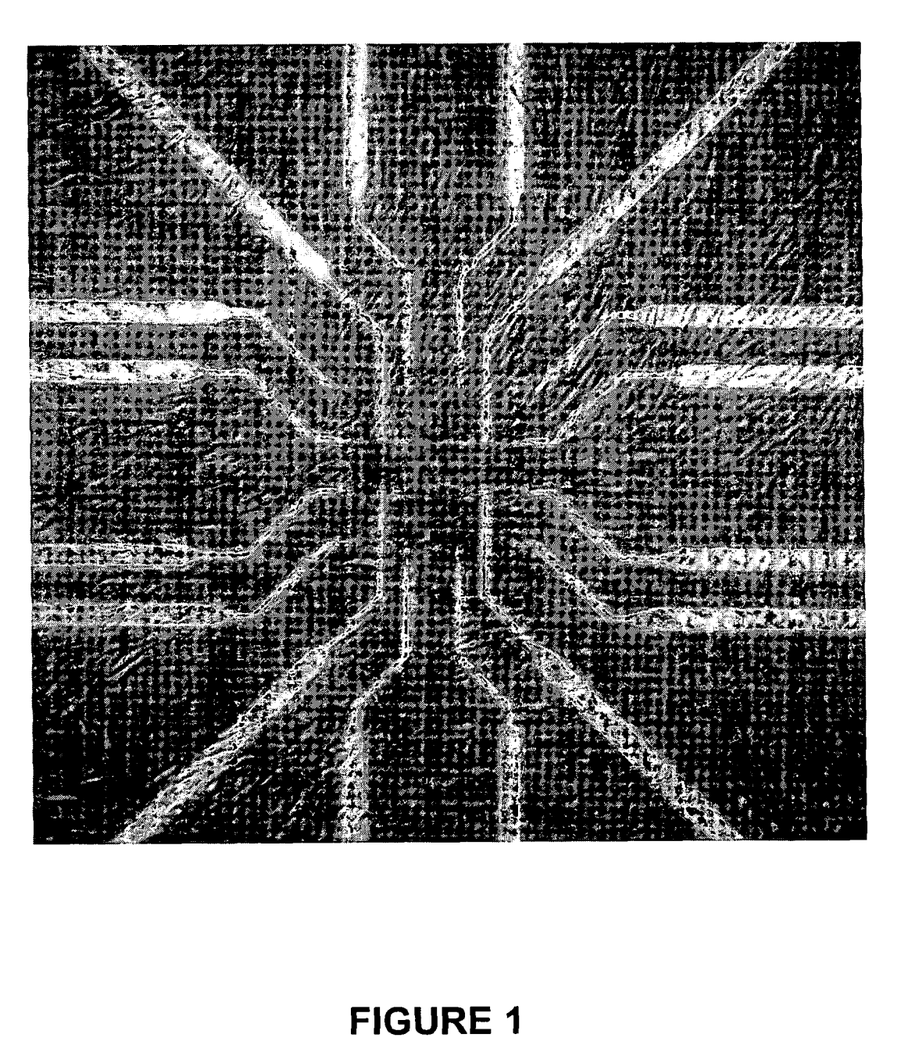
FIG. 1 is a surface view of the center region of one embodiment of a microarray, with living FT cells growing on the surface.
Figure 2:
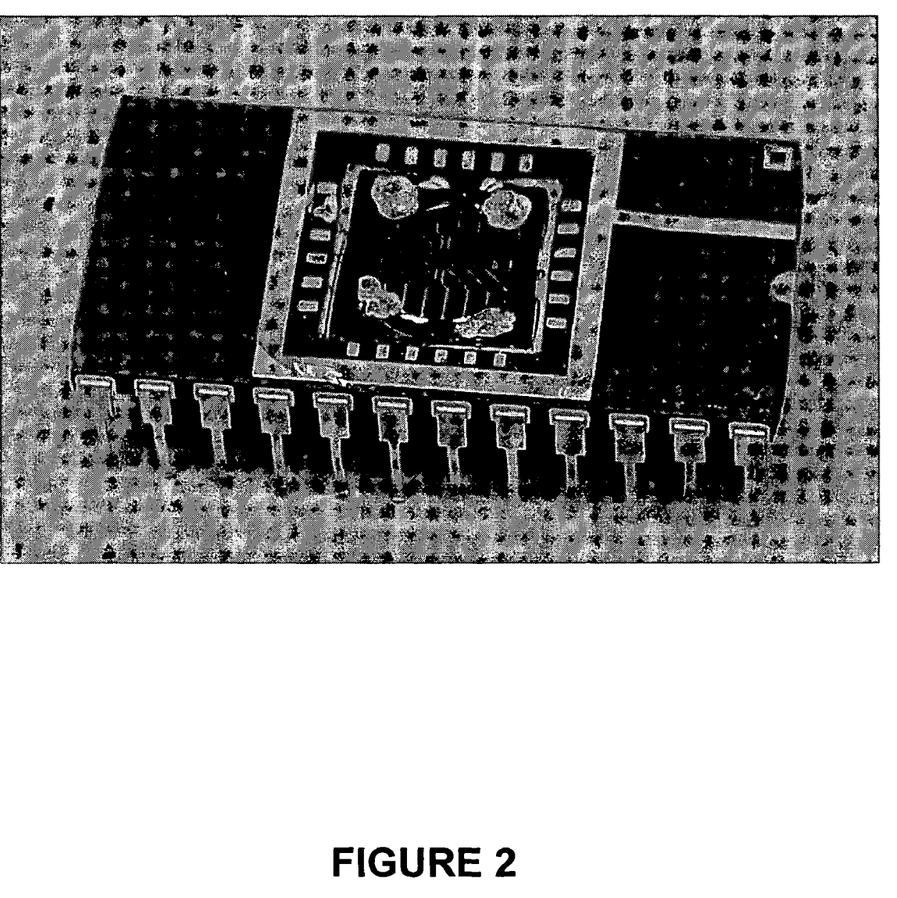
FIG. 2 is a photograph of one embodiment of a mounted microarray structure.

A microarray in accordance with the invention was fashioned having a polyimide surface overlaid with a plurality of Cr/Au electrodes of widths increasing in increments from 10 µm, to 20 µm, and then to 50 µm from center out (for example, see FIG. 1). The first step of the fabrication process was to spin a 4.3 µm layer of polyimide 2560 (HD Microsystems) onto a 4 inch p-type silicon wafer as follows. The wafer was first washed in acetone/isopropanol. Secondly, VM652 promoter was puddled on the wafer for 30 sec. before spinning at 2000 rpm for 30 sec. The wafer was then baked at 95° C. for 90 sec.

The polyimide 2560 was spun from 100 rpm to 500 rpm in 100 rpm increments, 30 sec. each, ramping at 100 rpm/second between each interval. After a final spin at 3000 rpm for 2 min, the polyimide layer was cured in the oven overnight according to the following schedule: the temperature was ramped from 50° C. to 200° C. over 50 min and kept at 200° C. for 30 min. Then the temperature was ramped from 200° C. to 350° C. over 50 min and kept at 350° C. for 60 min. Finally, the temperature was ramped slowly down to 15° C. overnight. Following coating and patterning of the wafer with photoresist, 30 nm Cr and 100 nm Au were deposited atop the polyimide by e-beam evaporation. After the liftoff process with photoresist remover, the electrodes, conducting traces, and contact pads were formed.

Prior to use, the microarray was mounted in a carriage; PDMS was used to hold the array in place and silver paste was used to form the electrical connections between the Cr/Au electrodes and the carriage electrodes.

In another embodiment, the microarray is fabricated with polydimethylglutarimide (PMGI) to support cell growth. The PMGI and the Cr/Au electrodes are applied to a layer of $SiO_2$.

Figure 5:
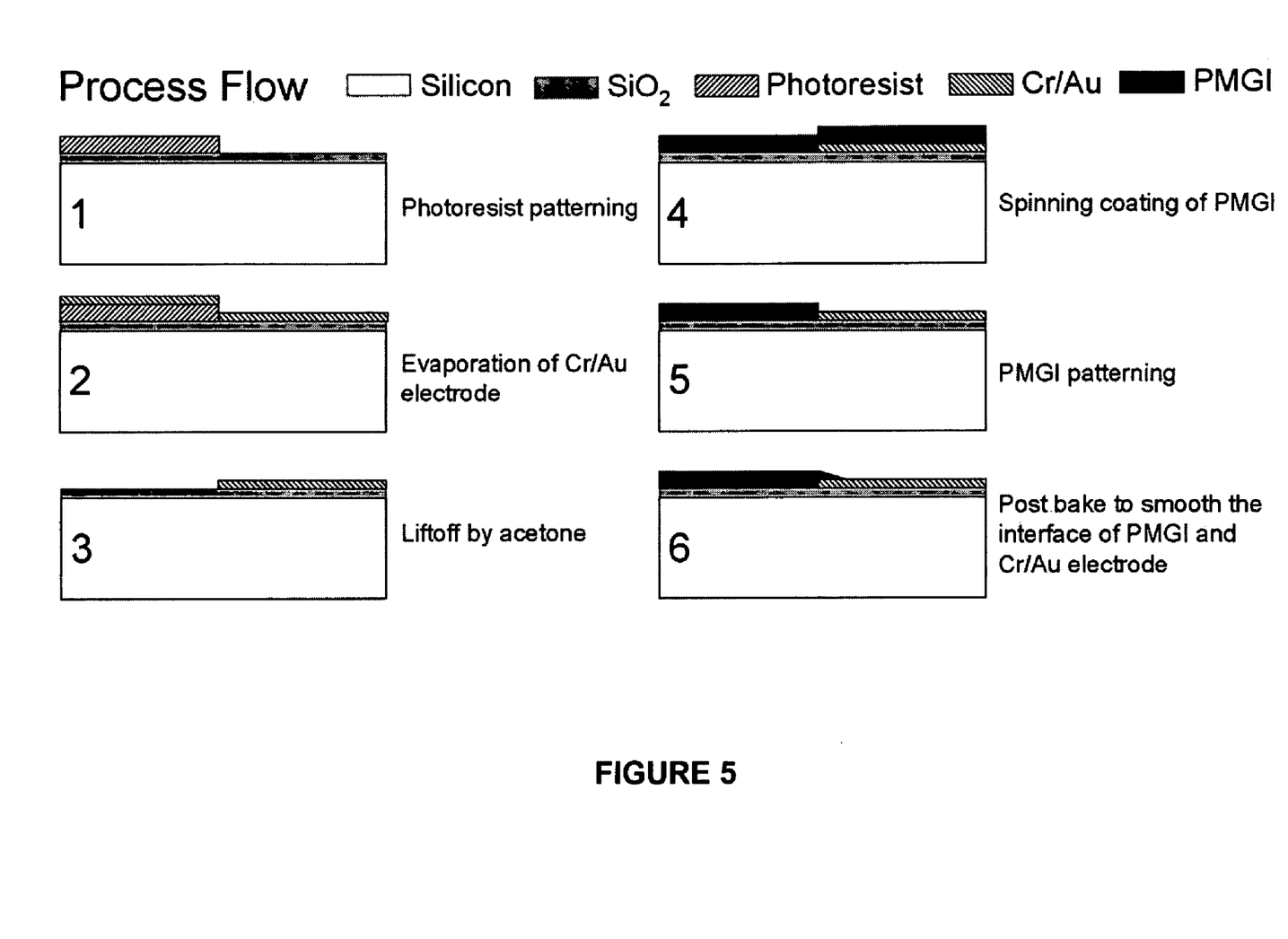
FIG. 5 is a schematic diagram of a process flow for fabrication of one embodiment of the microarray of the biosensor.

In this embodiment, PMGI can be patterned directly on the surface of the silicon wafer, allowing patterning of the Cr/Au electrodes directly onto the silicon between the spaces covered by the PMGI. The process flow for this embodiment is shown in FIG. 5. After the silicon is coated with $SiO_2$, a layer of photoresist is applied and patterned on the array according to the design (1). A layer of Cr/Au is then evaporated onto the surface (2), and the excess, which lies atop the photoresist, is lifted by acetone (3). A layer of PMGI is added by spin coating (4) and then patterned (5). Finally, the array is baked to smooth the interface between the PMGI and the Cr/Au electrode (6).

Figure 6:
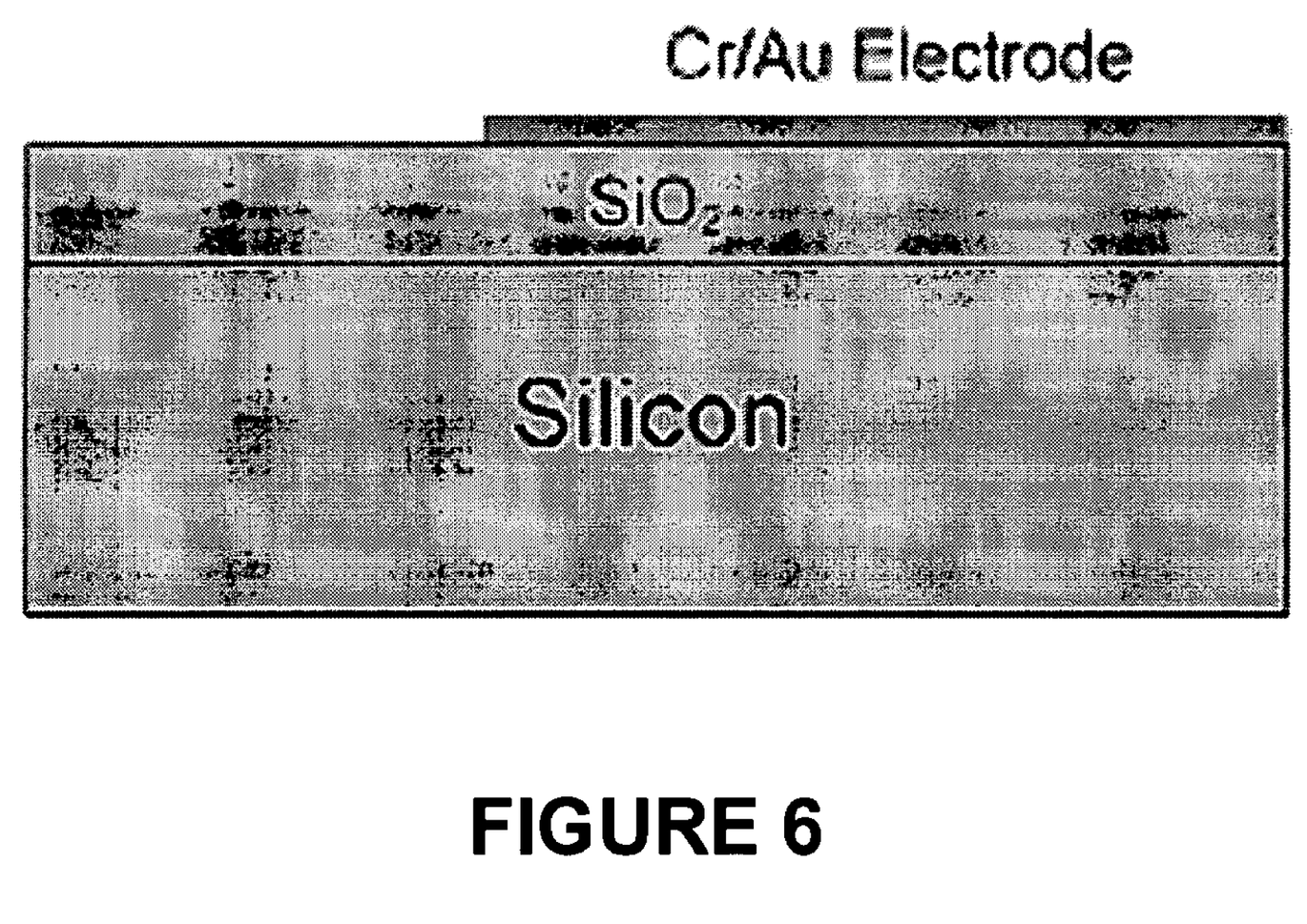
FIG. 6 is a schematic diagram of one embodiment of the microarray of the biosensor.

In yet another embodiment, electrodes were bonded directly onto the $SiO_2$. The cells were grown directly on the $SiO_2$, after cleaning. This embodiment is shown in FIG. 6.

The microarrays were sterilized with 70% ethanol prior to culturing cells on their surface.

Cell Culture and Cell Growth on the Surface of the Microarray

Any vertebrate cell that is 1) amenable to genetic manipulation, 2) secretes catecholamines or that secretes exogenous compounds taken up from the culture medium, i.e., can be "pre-loaded" and 3) that can be grown on the surface of a microarray is suitable for integration into the biosensor of the present invention. One cell line that is suitable for use in the present invention is rat PC12 cells (ATCC®, Manassas, Va., catalog number CRL-1721), pheochromocytoma cells derived from the adrenal medulla of the rat (*Rattus norvegicus*.)

Amphibian cells, in particular, are useful because they can be propagated at room temperature under ambient atmospheric conditions. Cells from amphibians such as *Rana catesbeiana* can also be kept dormant for prolonged periods at 4° C., properties that make these cells highly desirable for microarray applications. In one embodiment of the invention, an amphibian cell line derived from fibroblasts was used. These cells non-specifically endocytose substances from the medium and secrete them through $Ca^{2+}$-dependent, spontaneous quantal release. Hence, the secreted molecule can be selected by "pre-loading" the cells prior to exposure to analyte. This property in conjunction with the ability to recombinantly modify the cells to express G protein-coupled receptors (GPCR) is used to increase intracellular calcium to modulate the release of catecholamine or other oxidizable molecule upon binding of a specific ligand in a biosensor that detects this release electrochemically.

In one embodiment of the invention, amphibian fibroblasts were used. Examples of amphibian fibroblast cell lines suitable for practicing the invention include, but are not limited to, the FT cell line, derived from bullfrog, *Rana catesbeiana* (ATCC®, Manassas, Va., catalog number CCL-41). Examples of other suitable amphibian cells include, but are not limited to, tissues or cell lines derived from *Xenopus laevis* or *Rana catesbeiana*. Cells or cell lines derived from other poikilotherms that either synthesize oxidizable compounds or can be loaded with such compounds would also be suitable for the invention.

Cells, for example, FT cells, can be seeded directly onto the surface of the microarray, where they will grow until confluent. Ideally, to minimize the distance between the cell surface and the Cr/Au electrodes, cells should form a confluent or nearly confluent monolayer, that is, between 50 and 100%, preferably between 75 and 100%, more preferably between 90 and 100%, with near-100% confluence being most preferred, that brings them into direct contact with the electrodes. This obviates the need to pattern the growth of the cells to bring them into appropriate contact with the electrodes, as is the case with other microarrays in the art.

FT cells were maintained as stock cultures in minimum essential medium Eagle with 2 mM L-glutamine and Earle's BSS adjusted to contain 1.5 g/L sodium bicarbonate, 0.1 mM non-essential amino acids, and 1.0 mM sodium pyruvate supplemented with 10% double distilled water and 10% FBS, as previously described [Science 144: 1578, 1964]. For experimental treatments, FTs were trypsinized, washed with PBS, and precise counts of the number of cells were made using either a hemocytometer or an electronic cell counter (Beckman Coulter, Inc., Fullerton, Calif.).

Suitable media for culture of the amphibian cells includes the recommended ATCC® culture medium described above which is a $CO_2$ buffered medium. In an alternate embodiment, the microarray culture medium described below was developed which works in the absence of a $CO_2$ atmosphere. This facilitates growth of the FT cells on microarrays under ambient conditions.

To test whether FT cells would cover the electrodes, we seeded a packaged microarray with FT cells to 30% confluence. Prior to seeding, the arrays were sterilized with 70% ethanol and placed into plastic Petri dishes. After seeding the dishes were covered to prevent contamination and dessication. Cultures were then incubated at 22-23° C. under ambient atmospheric conditions. Generally, the cultures reached 100% confluence in two weeks, at which time the FT cells successfully covered the entire electrode surface at all the various widths, including at 50 µm. Significantly, this ability of the FT cells to cover the electrodes means that increasing the electrode surface to maximize current is feasible without interfering with cell growth. Moreover, once seeded, the FT cells will grow into the optimal configuration for recording without the need for special patterned polymers to direct them. In addition, having a confluent layer of cells cover the electrodes may help to insulate the electrodes from contact with test substances in the medium that might potentially interfere with recordings.

Use of G Protein-Coupled Receptors as a Chemical Sensor

The range of detectable compounds for the biosensor of the invention is expanded by transfecting the cells to be integrated into the biosensor with G protein-coupled receptors. Any G protein-coupled receptor that activates phospholipase C to raise intracellular calcium can be used as the ligand sensor. Examples include receptors for bombesin, gastrin releasing peptide, neuromedin B, angiotensin, bradkinin, anaphylatoxin, formyl peptide, interleukin 8, cholecystokinin, gastrin, endothelin 1, neurotensin, substance P, substance K, neuromedin K, oxytocin, vasopressin, thrombin, orexin (hypocretin), urotensin, prostaglandin F2-2, ATP, platelet activating factor, gonadotropin releasing hormone, thyrotropin releasing hormone, glutamate etc.

The receptor sequences to be transfected can be driven by a number of promoters, including but not limited to a cytomegalovirus (CMV) promoter, or a *Xenopus* cytoskeletal actin promoter. In some embodiments, where regulation of expression levels of the exogenous gene is required, the use of an inducible promoter system, such as a tetracycline inducible promoter system may be desirable.

In one embodiment of the invention, the mouse gastrin releasing peptide receptor is used for transfection. The nucleotide sequence of the receptor for mouse gastrin releasing peptide (mGPR-R) is known [Genbank Accession No. AH007139, Battey et al., *Molecular cloning of the bombesin/gastrin-releasing peptide receptor from Swiss 3T3 cells*. Proc Natl Acad Sci USA 88:395-399, 1991]. The GRP receptor functions by activating phospholipase C to raise intracellular calcium [Hellmich et al, 1997; Jian et al, 1999]; 3) and has a wide range of specific, well-characterized antagonists and agonists that are readily available for this receptor [Pradhan et al., *Identification of a unique ligand which has high affinity for all four bombesin receptor subtypes*. Eur J Pharmacol 343:275-287, 1998]. This receptor functions both in fibroblasts [Kusano et al., *Receptor-activated currents in mouse fibroblasts expressing transfected bombesin receptor subtype cDNAs*. Am J Physiol 265:C869-76, 1993], as well as in amphibian cells, for example, *Xenopus* 3 oocytes, where it activates a calcium-activated chloride channel in response to exposure to agonist [Shapira et al., *Distinguishing bombesin receptor subtypes using the oocyte assay*. Biochem Biophys Res Commun 176:79-86. 1991]. GRP-R belongs to the opsin class of G protein-coupled receptors (class IIIb), a class that includes a wide range of G protein-coupled receptors suitable for use in the present invention to detect other substances of interest. The ligand binding sites for this receptor within the protein are well characterized (Akeson et al, 1997; Tokita et al, 2001). This receptor and other similar receptors can be recombinantly modified by methods well known in molecular biology, including site-directed mutagenesis and domain swapping to create variants that detect other substances of interest.

Transfection of cells for use in the biosensor of the present invention may be achieved by techniques well know to those of skill in the art. For preparation of stably transfected cells, full-length cDNA encoding the desired G protein-coupled receptor (e.g., mGRP-R) is inserted, along with sequences encoding an appropriate promoter, into a vector suitable for transfecting eukaryotic cells. This is accomplished using conventional cloning methods that are routinely used in the art. One such vector is the pIRES2-EGFP vector (Clontech, BD Biosciences, Palo Alto, Calif.). pIRES2-EGFP contains an internal ribosome entry site (IRES) which permits expression of both the gene of interest, in the case of the present invention, a GPCR, and an enhanced green fluorescent protein (EGFP) gene to be translated from a single bicistronic mRNA. pIRES2-EGFP is designed for the rapid identification and efficient enrichment of transfected cells by fluorescence microscopy, flow cytometry or other methods. This vector can be used to obtain stably transfected cell lines without time-consuming drug and clonal selection. Additionally, pIRES2-EGFP contains a $Kan^R/Neo^R$ cassette which allows antibiotic selection by kanamycin and neomycin in bacteria and FT cells, respectively. It also contains a cytomegaloviral promoter (CMV), which is suitable for obtaining expression in FT and PC-12 cells. Other promoters appropriate for expression in FT cells include, but are not limited to, a *Xenopus borealis* cytoskeletal actin promoter.

Following transfection, FT cells are transferred to medium containing neomycin following the recommended protocols of the manufacturer of pIRES2 vectors. Over several weeks of culturing, only those cells that stably express neomycin survive. Cells are subsequently tested for expression of the receptor (e.g., mGRP-R) using immunofluorescence and an antibody directed against the receptor.

In another embodiment, stably transfected cell lines are created using a retroviral expression system, for example, Pantropic Retroviral Expression System (Clontech). This system uses an envelope glycoprotein, VSV-G, which infects cells independently of a cell receptor. The GP2-293 cell line is used as a host to generate viral particles for introducing exogenous genes in the cells to be used in the biosensor.

The GP2-293 cells are cotransfected with two plasmids: one that encodes the VSV-G glycoprotein, and the other can be any retroviral expression plasmid, for example, pLNCX2, containing the desired gene, in this case a GPCR such as mGRP-R. The retroviral expression plasmid.

Cells that have been stably transfected are propagated and aliquots frozen and stored in liquid nitrogen for future use.

For culture on the microarray, cells are prepared in microarray culture medium, as described below and are plated at 10-30% confluence. The cells reach 100% confluence in approximately two weeks, when grown at 22-23° C.

Microarray Culture Medium
  612 ml L-15 defined medium (Invitrogen/GIBCO, Carlsbad Calif.) with 5 U/ml penicillin and 51 μg/ml streptomycin
  304 ml tissue culture grade water
  148 ml fetal bovine serum (Invitrogen/GIBCO, Carlsbad Calif.)
  8 ml 200 mM L-glutamine Pre-Loading of Cells The principle of calcium-dependent vesicular exocytosis (secretion) of compounds loaded into non-neuronal cells, including fibroblasts, is well known to those of skill in the art. For example, exocytosis was originally monitored using a patch clamped *Xenopus* myocyte, which expresses its own acetylcholine receptors, to detect release of acetylcholine loaded into these cells from the medium (Dan and Poo, 1992). This release can be stimulated by raising intracellular calcium from multiple cell types in addition to the frog myocytes. These cell types include mammalian fibroblasts [Poo et al., *Calcium-dependent vesicular exocytosis: from constitutive to regulated secretion*. Cold Spring Harbor Symposia on Quantitative Biology 60:349-359 1995], and frog FT cells [Chang et al., *Constitutive secretion of exogenous neurotransmitter by nonneuronal cells: implications for neuronal secretion*. Biophysical J 75:1354-1364 1998]. In addition, the ratio of the amount of secretion that is released by the calcium-dependent mechanism over that released constitutively can be enhanced by transfecting cells with synaptotagmin, a calcium sensing protein involved in exocytosis [Morimoto, 1995]. Not only acetylcholine, but also a wide variety of substances applied exogenously to the cells for example, horseradish peroxidase [Morimoto et al., *Calcium-dependent transmitter secretion from fibroblasts: modulation by synaptotagmin I*. Neuron 15:689-696. 1995] and $^{14}C$-sucrose [Chang et al., *Constitutive secretion of exogenous neurotransmitter by non-neuronal cells: implications for neuronal secretion*. Biophysical J 75:1354-1364 1998], are released in this manner. In practicing the present invention, the cells were loaded with catecholamines, which can be readily detected by amperometric recording through the electrodes on our microarrays.

Detection of Current

The readout of GPCR activation is the detection of secreted catecholamines. Amperometry, recording the Faradaic current at a fixed potential is the preferred method for measuring quantal catecholamine release because it offers maximal time resolution.

Without wishing to be bound by theory, the following calculations highlight the parameters that influence the amount of current produced on the microarrays of the invention. In original studies of ACh release from FT cells [Chang et al., 1999], cells were loaded with 40 mM acetylcholine and recordings were made through myocytes manipulated into the vicinity of the FT cells. In these experiments, a single release event, representing the ACh content of a single vesicle, produced a post synaptic current in the myocyte of 240±16 pA. Vesicular release of 5,000 ACh molecules produces an ACh receptor current of 5 pA [Levitan and Kaczmarek, 2002]. Consequently, we can estimate the number of ACh molecules released during a single release event from preloaded FT cells:

$$240\ pA \times 5{,}000\ ACh\ \text{molecules}/5\ pA = 2.4 \times 10^5\ ACh\ \text{molecules} \qquad \text{Equation 1}$$

Because uptake and release from FT cells is non-specific to the loaded compound, it is reasonable to assume that the amount of a compound released by vesicles is linearly related to the amount present in the culture medium. We thus estimated that FT cells loaded with 10 mM norepinephrine (NE) will release approximately $6 \times 10^4$ NE molecules per vesicle. Since oxidation of each molecule of NE releases 2 electrons, this amount of NE should produce $1.2 \times 10^5$ electrons, within the linear range of the electrodes. Stimulation of the ATP receptor produced approximately 52 release events per minute from a 10 µm² surface area of FT cell. Assuming that our electrodes capture nearly 100% of the NE molecules released from the surface of the FT cells in contact with the electrode, an assumption that is justified by the close proximity of the cells to the electrode as well as results from well recordings made from chromaffin cells, we estimated the amount of current generated by release of NE from a 10 µm² area of ATP-stimulated FT cells to be:

$$(52\ \text{events}/60\ \text{sec}) \times (1.2 \times 10^5\ \text{electrons}) \times (1.6 \times 10^{-19}\ \text{Coulombs/electon}) = 0.02\ pA \qquad \text{Equation 2}$$

The total current produced on an electrode is then given by the area of the electrode covered by the FT cells:

$$I_{total} = \text{Electrode area}\ (\mu m^2) \times (0.02\ pA/10\ \mu m^2) \times (\text{Fraction of the electrode covered by FT cells}) \qquad \text{Equation 3}$$

At 100% confluence and an electode area of 105 µm², $I_{total}$ should be 0.2 nA per electrode, which is reasonably close to the value of 800 pA empirically obtained.

Figure 7:
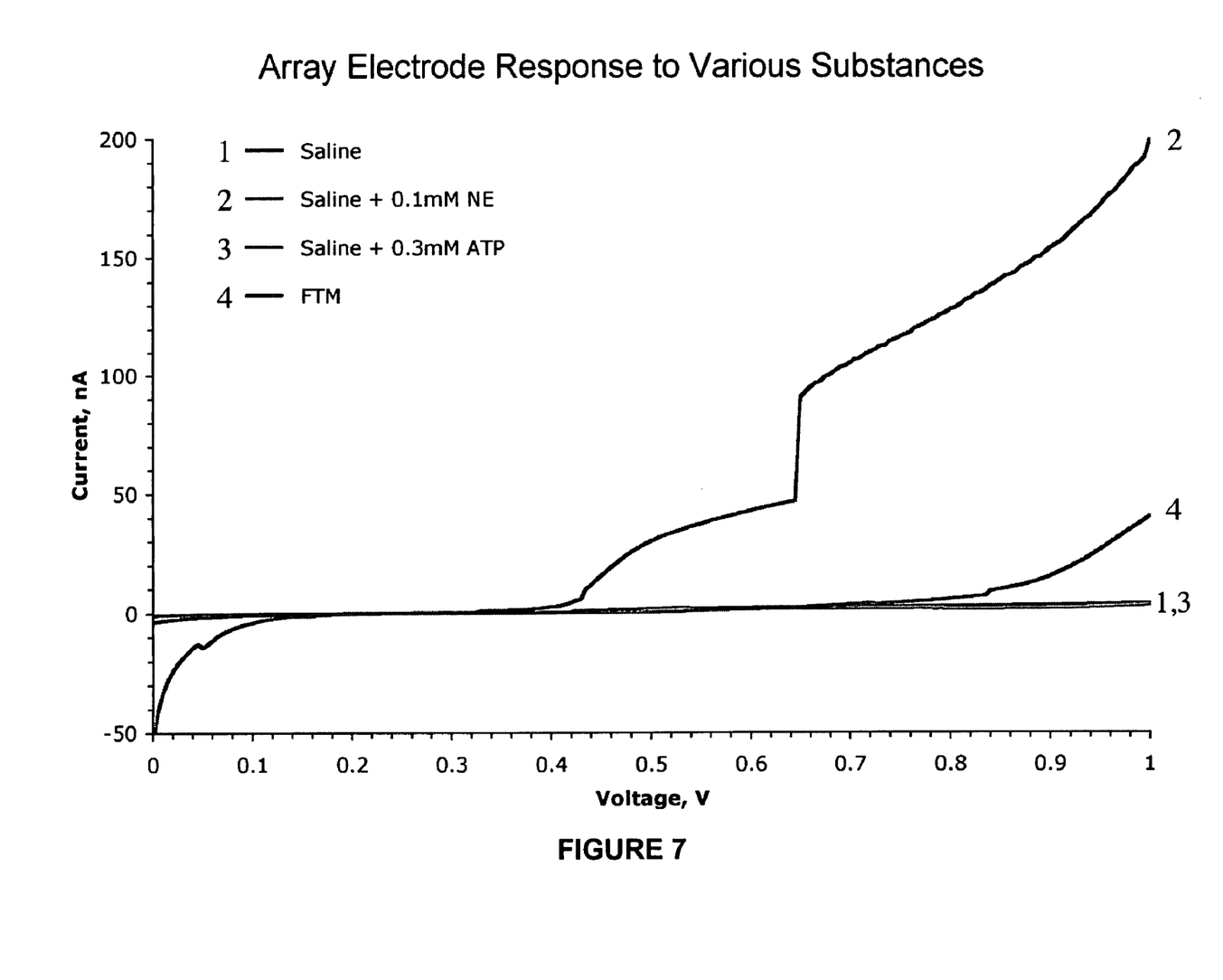
FIG. 7 is a graph showing the array electrode response to various substances including saline, 0.1 mM norepinephrine (NE), 0.3 mM ATP and FT culture medium.

Baseline response properties of the microarray of the invention were tested in the absence of cells to determine whether any components of the media and test solutions would interfere with measurements. Currents were measured from a single electrode as the different solutions were added and voltages were increased from 0-1V. The results are shown in FIG. 7A. 100 µM norepinephrine (NE) produced a measurable current (2), which increased between 0.4 and 1 V. The discontinuity at 625 mV represents the threshold of release for the second of the two electrons released by the voltage induced oxidation of NE. Neither saline (1) nor the application of 300 µM ATP (3) produced measurable currents. The culture medium in which the cells are cultured began to produce a small measurable current (4) at voltages exceeding 700 mV.

Figure 8:
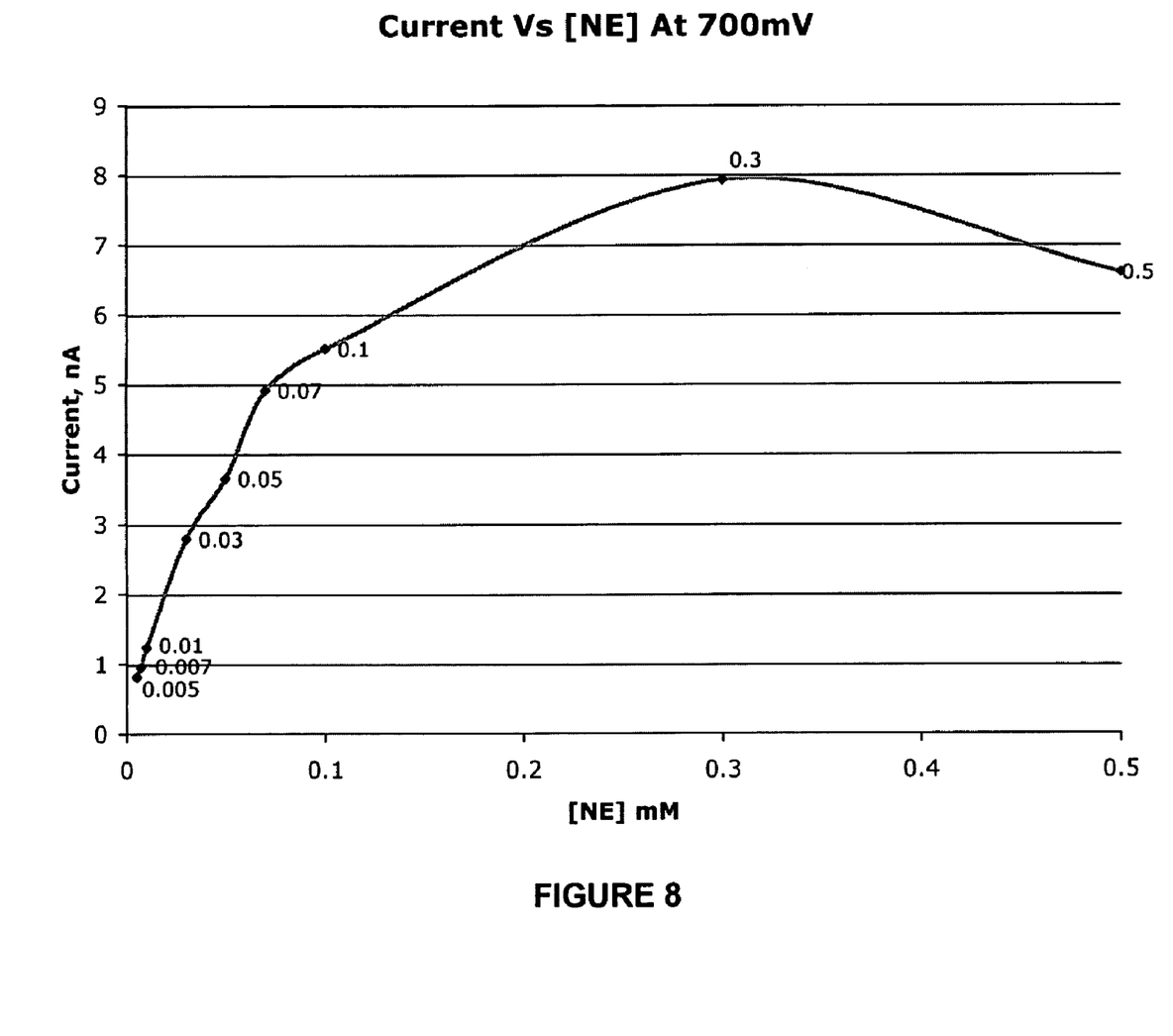
FIG. 8 is a graph showing the concentration of norepinephrine at which current (nA) is optimal at 700 mV.

At 700 mV, the current released by the oxidation of norepinephrine increased monotonically from 0 to 300 µM, and then began to decline. This is shown in FIG. 8.

A microarray containing a confluent growth of FT cells was subsequently tested. To test the response properties of the cells to ATP (0.3 mM), microarrays with confluent cultures of cells were measured prior to preloading with NE. Then, cells were pre-loaded with varying concentrations of NE and ATP was reapplied.

The cells can be washed, pre-loaded again, and stimulated with ATP, a more specific P2 receptor agonist, for example, UTP, ADP, MRS2365, INS37217; or ATP mixed with an antagonist of P2 receptors (for example, various pyridoxal phosphate derivatives) to specifically block the ATP P2Y GPCR.

Figure 9:
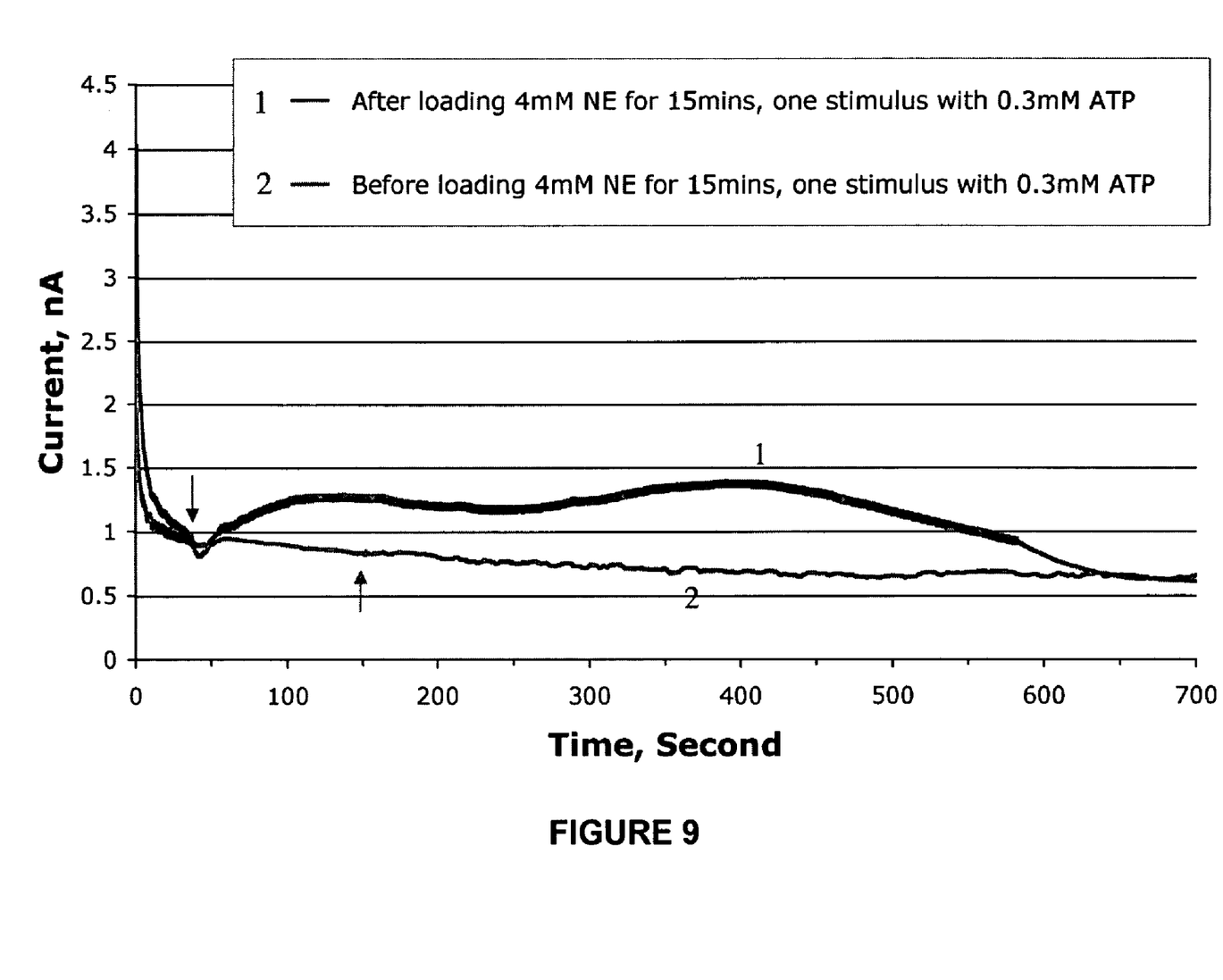
FIG. 9 shows the effect on current of pre-loading the cells with 4 mM norepinephrine prior to exposure to 0.3 mM ATP.

Current was recorded from a single electrode held at 700 mV as ATP was added to the FT medium to a final concentration of 300 µM (FIG. 9, addition is marked by the arrows.) Recordings made from cultures stimulated after preloading cells in 4 mM NE in FT medium for 15 min elicited a current with a peak of approximately 800 pA above baseline lasting for approximately 9-10 min (trace 1). The magnitude of this current was comparable to the expected value based on the theoretical calculations discussed above; however, the length of the response was somewhat longer than that described elsewhere—9-10 min as opposed to 4 min. Not wishing to be bound by theory, we believe that this difference reflects a population response rather than the response of a single cell.

To increase the reliability of the measurements, one may raise the current to between 10 and 100 nA. This may be done by expanding the area of microarray surface occupied by the electrodes, by increasing the amount of NE released by the cells or both.

Figure 10:
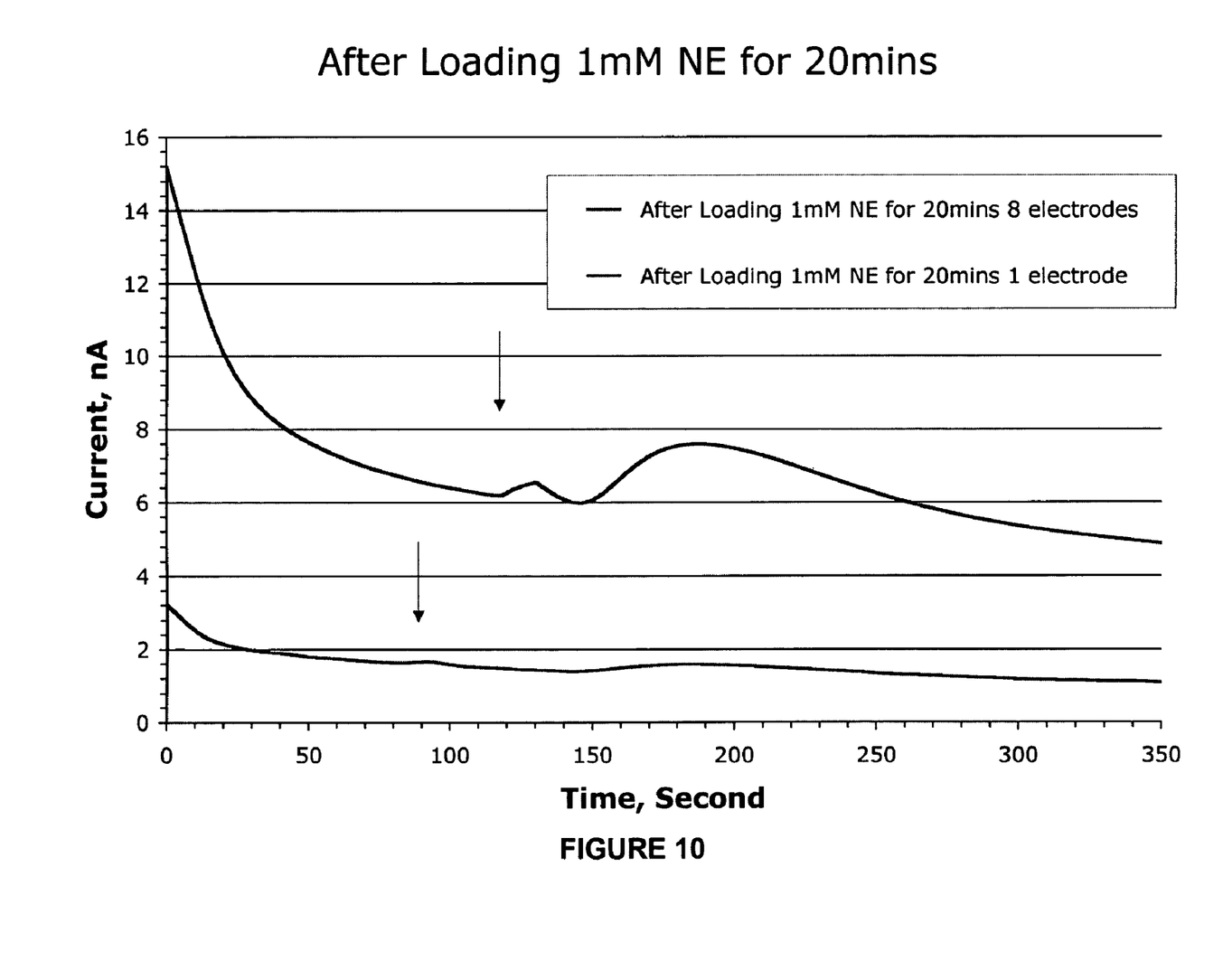
FIG. 10 is a comparison of the current detected using 1 electrode versus 8 electrodes.

In FIG. 10, a comparison of the current from single versus multiple electrodes is shown. Current traces collected after loading with 1 mM norepinephrine, upon stimulation with ATP at the indicated times (downward arrows) The upper trace represents the current collected from 8 electrodes; the lower trace represents the current measured from as single electrode.

In the cell-based sensors of the invention, the cellular components of the signaling pathway are intact; such sensors, therefore, can readily provide the basis for high throughput screening of drugs in a physiologically relevant context. Such devices are invaluable for detecting biotoxic compounds and for characterizing cellular responses to drugs targeted at GPCRs or their intracellular signaling pathways.

LITERATURE CITED

1. Akeson M, E Sainz, S A Mantey, R T Jensen, J F Battey (1997) Identification of four amino acids in the gastrin-releasing peptide receptor that are required for high affinity agonist binding. J Biol Chem 272:17405-9.
2. Battey J F, J M Way, M H Corjay, H Shapira, K Kusano, R Harkins, J M Wu, T Slattery, E Mann, R I Feldman (1991) Molecular cloning of the bombesin/gastrin-releasing peptide receptor from Swiss 3T3 cells. Proc Natl Acad Sci USA 88:395-399.
3. Chang S, G Romain, T Morimoto, M O'Donoghue, S Popov (1998) Constitutive secretion of exogenous neurotransmitter by nonneuronal cells; implications for neuronal secretion. Biophysical J 75:1354-1364.
4. Chen P, B Xu, N Tokranova, X Feng, J Castracane, K D Gillis (2003) Amperometric detection of quantal catecholamine secretion from individual cells on micromachined silicon chips. Anal Chem 75:518-524.
5. Feng X, B. G. Szaro, S. Baselmans, A. Gracias, N. Tokranova, B. Xu and J. Castracane, "Microfabricated Devices for Bio-Applications", to be published, Microfluidics, BioMEMS and Medical Microsystems, (2005).
6. Feng X, N. Tokronova, B. Xu, B. G. Szaro and J. Castracane, "Study of Cell Secretion Using MEMS-Based Arrays", Micromachining and Microfabrication, Vol. 5345 (2004).
7. Hellmich M R, J F Battey, J K Northup (1997) Selective reconstitution of gastrin-releasing peptide receptor with G alpha q. Proc Natl Acad Sci USA 94:751-756.
8. Kusano K, H Gainer, J F Battey, Z Fathi, E Wada (1993) Receptor-activated currents in mouse fibroblasts expressing transfected bombesin receptor subtype cDNAs. Am J Physiol 265:C869-76.

9. Jian X, E Sainz, W A Clark, R T Jensen, J F Battey, J K Northup (1999) The bombesin receptor subtypes have distinct G protein specificities. J Biol Chem 274:11573-11581.
10. Marilley D, A Mahfoudi, W Wahli (1994) Gene transfer into *Xenopus* hepatocytes: transcriptional regulation of the nuclear receptor superfamily. Molecular and Cellular Endocrinology 101:227-236.
11. Morimoto T, S Popov, K M Buckley, M Poo (1995) Calcium-dependent transmitter secretion from fibroblasts: modulation by synaptotagmin I. Neuron 15:689-696.
12. Poo M, Y Dan, H Song, T Morimoto, S Popov (1995) Calcium-dependent vesicular exocytosis: from constitutive to regulated secretion. Cold Spring Harbor Symposia on Quantitative Biology 60:349-359.
13. Pradhan T K, T Katsuno, J E Taylor, S H Kim, R R Ryan, S A Mantey, P J Donohue, H C Weber, E Sainz, J F Battey, D H Coy, R T Jensen (1998) Identification of a unique ligand which has high affinity for all four bombesin receptor subtypes. Eur J Pharmacol 343:275-287.
14. Shapira H, E Wada, J F Battey, R T Jensen, D H Coy, K Kusano (1991) Distinguishing bombesin receptor subtypes using the oocyte assay. Biochem Biophys Res Commun 176:79-86.
15. Tokita K, T Katsuno, S J Hocart, D H Coy, M Llinares, J Martinez, R T Jensen (2001) Molecular basis for selectivity of high affinity peptide antagonists for the gastrin-releasing peptide receptor. J Biol Chem 276:36652-36663.

The invention claimed is:

1. A biosensor comprising:
    (a) a microarray having an even surface adapted to support cell growth, and having metal electrodes patterned on a first portion of said even surface of said microarray;
    (b) an adherent monolayer of amphibian secretory cells that express a G protein-coupled receptor, wherein the cells of said monolayer are attached to a second portion of the surface of the microarray adjacent to the first portion upon which the electrodes are patterned and form a confluent or nearly confluent monolayer that is extended directly over said electrodes, and in response to ligand binding to the G-protein-coupled receptor, the cells secrete a molecule that is oxidized on the electrode generating a detectable current; and
    (c) a detector adapted to detect current generated by oxidation of the secreted molecule on the electrodes of the microarray.

2. The biosensor of claim 1 wherein the cells secrete catecholamines.

3. The biosensor of claim 1 wherein the cells are loaded with catecholamines prior to exposure to a sample to be tested.

4. The biosensor of claim 1, wherein the cells are FT cells.

5. The biosensor of claim 1, wherein said electrodes are made of a material selected from the group consisting of gold, platinum, palladium, chromium, molybdenum, iridium, tungsten, tantalum and titanium.

6. The biosensor of claim 5, wherein said electrodes are made of Cr/Au.

7. The biosensor of claim 1, wherein the microarray comprises polyimide applied to a silicon substrate and metal electrodes are patterned thereon.

8. The biosensor of claim 1, wherein the microarray comprises polydimethylglutarimide applied to a silicon substrate coated with $SiO_2$ subsequent to electrode patterning.

9. The biosensor of claim 1, wherein said cells are grown directly on the surface of said microarray.

10. The biosensor of claim 1, wherein said cells are grown until a confluent or nearly confluent monolayer is formed.

11. The biosensor of claim 1, wherein said monolayer is 50-100% confluent.

12. The biosensor of claim 1, wherein said monolayer is 75-100% confluent.

13. The biosensor of claim 1, wherein said monolayer is 90-100% confluent.

14. The biosensor of claim 1, wherein said monolayer is 95-100% confluent.

15. A method of measuring an analyte in a biological sample comprising:
    (a) exposing a biosensor comprising:
        (i) a microarray having an even surface adapted to support cell growth, and having metal electrodes patterned on a first portion of said even surface of said microarray;
        (ii) an adherent monolayer of amphibian secretory cells that express a G protein-coupled receptor, wherein the cells of said monolayer are attached to a second portion of the surface of the microarray adjacent to the first portion upon which the electrodes are patterned and form a confluent or nearly confluent monolayer that is extended directly over said electrodes, and in response to ligand binding to the G-protein-coupled receptor, the cells secrete a molecule that is oxidized on the electrode generating a detectable current; and
        (iii) a detector adapted to detect current generated by oxidation of the secreted molecule on the electrodes of the microarray,
    to a biological sample; and
    (b) detecting a signal generated as the result of exposure of the biosensor to the biological sample, wherein said signal is indicative of the amount of analyte in the biological sample.

* * * * *